United States Patent [19]
Sommers et al.

[11] Patent Number: 6,105,578
[45] Date of Patent: Aug. 22, 2000

[54] EQUIPMENT DRAPE FOR USE WITH AN INTERVENTIONAL MAGNETIC RESONANCE IMAGING DEVICE

[75] Inventors: Jay R. Sommers, Marietta, Ga.; John W. Frankland, Beckenham, United Kingdom; Chris Vetsch, Bremgarten, Switzerland

[73] Assignee: Kimberly-Clark Worldwide, Inc., Neenah, Wis.

[21] Appl. No.: 08/807,089

[22] Filed: Feb. 27, 1997

[51] Int. Cl.⁷ .................................................. A61B 19/00
[52] U.S. Cl. ........................................... 128/849; 128/853
[58] Field of Search ..................... 128/849–856

[56] References Cited

U.S. PATENT DOCUMENTS

| | | | |
|---|---|---|---|
| 3,263,680 | 8/1966 | Morgan | 128/853 |
| 3,276,944 | 10/1966 | Levy . | |
| 3,338,992 | 8/1967 | Kinney . | |
| 3,341,394 | 9/1967 | Kinney . | |
| 3,364,928 | 1/1968 | Creager | 128/853 |
| 3,502,538 | 3/1970 | Petersen . | |
| 3,502,763 | 3/1970 | Hartmann . | |
| 3,542,615 | 11/1970 | Dobo et al. . | |
| 3,692,518 | 9/1972 | Dorschner et al. . | |
| 3,849,241 | 11/1974 | Butin et al. . | |
| 3,930,497 | 1/1976 | Krebs et al. . | |
| 4,041,942 | 8/1977 | Dougan et al. . | |
| 4,340,563 | 7/1982 | Appel et al. . | |
| 4,569,341 | 2/1986 | Morris . | |
| 4,663,220 | 5/1987 | Wisneski et al. . | |
| 5,002,068 | 3/1991 | Provell . | |
| 5,197,492 | 3/1993 | Ravis, Jr. et al. . | |
| 5,381,802 | 1/1995 | Schwartzenfeld . | |
| 5,417,225 | 5/1995 | Rubenstein et al. . | |
| 5,498,463 | 3/1996 | McDowall | 128/859 |
| 5,578,359 | 11/1996 | Forbes et al. . | |
| 5,647,376 | 7/1997 | Thompson | 128/855 |

FOREIGN PATENT DOCUMENTS

| | | |
|---|---|---|
| 803714 | 1/1969 | Canada . |
| 0280839 | 9/1988 | European Pat. Off. . |
| 0291481 | 11/1988 | European Pat. Off. . |
| 8711722 | 1/1988 | Germany . |
| 4236160 | 5/1994 | Germany . |

OTHER PUBLICATIONS

NRL Report 5265, Lawrence, K. D., Lucas, R. T. and Young, J. A., entitled, "An Improved Device For The Formation of Superfine, Thermoplastic Fibers", U.S. Naval Research Laboratory, pp. 1–8, Feb. 59.

NRL Report 4364, Wente, W. A., Boone, E. L. and Fluharty, C. D., entitled, "Manufacture of Superfine Organic Fibers", Naval Research Laboratory, pp. 1–15, May 25, 1954.

*Primary Examiner*—Michael A. Brown
*Attorney, Agent, or Firm*—Jones & Askew, LLP

[57] ABSTRACT

The present invention is directed to novel equipment drapes for use with an Interventional Magnetic Resonance Imaging (IMRI) device. An IMRI device enables medical personnel to obtain magnetic resonance imaging data on a patient and, at the same time, perform surgery on the patient. An IMRI device requires specialty equipment. The present invention is directed to one form of specialty equipment, equipment drapes. Equipment drapes of the present invention have a U-shape or rectangular shape and are attached to the IMRI machine to maintain a sterile field and to provide a barrier against fluids escaping from a surgery patient. In one embodiment, the present invention discloses an equipment drape having a U-shape with a retractable flap positioned with the "U" portion of the drape. In a further embodiment, the present invention discloses an equipment drape having a U-shape with a retractable pouch positioned with the "U" portion of the drape. The pouch is designed to temporarily house surgical instruments during a surgical procedure. Another embodiment of the present invention is directed to an equipment drape set which includes four equipment drapes attached to the IMRI device and positioned such that at least a portion of a patient within the IMRI device is partially separated from the surgical team.

20 Claims, 3 Drawing Sheets

EQUIPMENT DRAPE FOR USE WITH AN INTERVENTIONAL MAGNETIC RESONANCE IMAGING DEVICE

FIELD OF THE INVENTION

The present invention is directed to novel equipment drapes for use with an Interventional Magnetic Resonance Imaging (IMRI) device. The present invention is directed to one specialty piece of equipment, an equipment drape having a U-shape, which is attached to the IMRI machine and provides a barrier against fluids escaping from a patient while maintaining a sterile field.

BACKGROUND OF THE INVENTION

Conventional Magnetic Resonance Imaging (MRI) devices consist of a tubular structure wherein a patient is moved into a magnetic field created by and within the MRI device. Imaging data of specific regions within a patient's body are produced by the MRI device. The imaging data is used by a medical team to determine if surgery is necessary, and if so, the degree of surgery necessary. Once surgery begins, a doctor can not obtain additional imaging data on the patient, unless surgery is halted for a period of time so that the patient can once again be placed within the MRI device. Real-time imaging data is not possible using conventional MRI devices.

To overcome the shortcomings of conventional MRI devices, Interventional Magnetic Resonance Imaging (IMRI) devices were developed. IMRI devices enable doctors to obtain real-time imaging data on a patient during the surgical procedure.

IMRI devices comprises two magnet halves, both of which are tubular in shape and positioned apart from one another. A magnetic field is created within the area between the magnet halves. A patient is transported through a first tubular half into a surgery zone and optionally at least partially through the second half. As imaging data is produced and displayed on overhead monitors, surgeons are able to use the real-time imaging data as the surgeons perform a surgical procedure.

The new design of the IMRI device and the ability to perform surgery in a surgery zone between portions of the IMRI device lead to the realization that an equipment drape for use with the IMRI device was needed. However, existing drapes were found to be inadequate. One such drape, MRI-Order No. 146D86, produced by the Baxter Corporation, Deerfield, IIL., was found to be too narrow to adequately cover the magnet, too short to provide a barrier between the surgery zone and the surgeons, too narrow for the patient to pass through, and not capable of sufficiently attaching to the device.

There exists a need in the art for an equipment drape specifically designed to match the dimensions of the IMRI device. Also, an equipment drape is needed which will provide a barrier between a surgery zone and the surgeon. Further, an equipment drape is needed which will provide an opening for the patient to pass through as the patient is transported into the IMRI device without contaminating the sterile field. Moreover, an equipment drape is needed which will securely attach to the IMRI device.

SUMMARY OF THE INVENTION

The present invention is directed to novel equipment drapes for use with an Interventional Magnetic Resonance Imaging (IMRI) device. An IMRI device enables medical personnel to obtain magnetic resonance imaging data on a patient and, at the same time, perform surgery on the patient. An IMRI device requires specialty equipment for safe and clean operation of the IMRI device. The present invention is directed to specialty equipment for use with an IMRI device. One such piece of specialty equipment comprises an equipment drape having a U-shape, which is attached to the IMRI machine and provides a barrier against fluids escaping from a patient. In a further embodiment, the present invention discloses an equipment drape having a U-shape with a flap portion or retractable pouch positioned with the "U" portion of the drape. The pouch is designed to temporarily house surgical equipment during a surgical procedure. Another embodiment of the present invention is directed to an equipment drape set, including four equipment drapes attached to the IMRI device and positioned such that at least a portion of a patient within the IMRI device is partially separated from the surgical team.

In one embodiment of the present invention, an equipment drape comprises a U-shape sheet having a peripheral edge, wherein the peripheral edge includes an outer upper edge, two outer side edges, two outer lower edges, and two inner side edges. Optionally, the drape further comprises a flap portion which extends downward from a central portion of the drape, between the two inner side edges. The drape also has an adhesive strip along at least a portion of the peripheral edge. Desirably, the adhesive strip is along the entire peripheral edge of the drape except for the lower edge of the flap, if present.

In another embodiment of the present invention, an equipment drape is disclosed which comprises a U-shape sheet having a peripheral edge and an adhesive strip along at least a portion of the peripheral edge as above. In this embodiment of the present invention, the drape further comprises a pouch integrally connected to the U-shape sheet. The pouch extends from a central portion of the drape, between the two inner side edges, and has a pouch opening facing toward the sheet.

In another embodiment of the present invention, an equipment drape set is produced by attaching four equipment drapes to the IMRI device such that at least a portion of a patient within the IMRI device is partially separated from the surgical team. The four drapes include a U-shaped equipment drape, a U-shaped equipment drape having a flap or pouch, and two rectangular drapes, each of which are positioned between the U-shaped equipment drapes to form the surgery zone.

The equipment drapes of the present invention can be made from a variety of materials including, but not limited to, woven fabrics, nonwoven fabrics, knit fabrics, films, and combination thereof. Desirably, the equipment drapes of the present invention are formed from one or more layers of nonwoven fabric. More desirably, the equipment drapes comprise a spunbonded or spunlaced fabric. Most desirably, the equipment drapes comprise a spunbonded/meltblown/spunbonded laminate.

The fibrous material used to form the webs above include natural fibers, synthetic fibers, and combinations thereof. The choice of fibers depends upon, for example, fiber cost and the desired properties, e.g., liquid resistance, vapor permeability or lint generation, of the finished drape. For example, suitable fibrous materials may include, but are not limited to, natural fibers such as cotton, linen, jute, hemp, cotton, wool, wood pulp, etc. Similarly, regenerated cellulosic fibers such as viscose rayon and cuprammonium rayon, modified cellulosic fibers, such as cellulose acetate, or synthetic fibers such as those derived from polyolefins, polyesters, polyamides, polyacrylics, etc., alone or in combination with one another, may likewise be used. Blends of one or more of the above fibers may also be used if so desired.

It has been found that nonwovens formed from natural fibers, alone or in combination with at least one of polyolefin, polyester and polyamide fibers, are particularly well-suited for the equipment drapes of the present invention.

The equipment drapes of the present invention satisfy the need for suitable equipment drapes for use with the recently developed IMRI device. A detailed description of equipment drapes and their use in connection with an IMRI device is provided below.

DETAILED DESCRIPTION OF THE INVENTION

Figure 1:
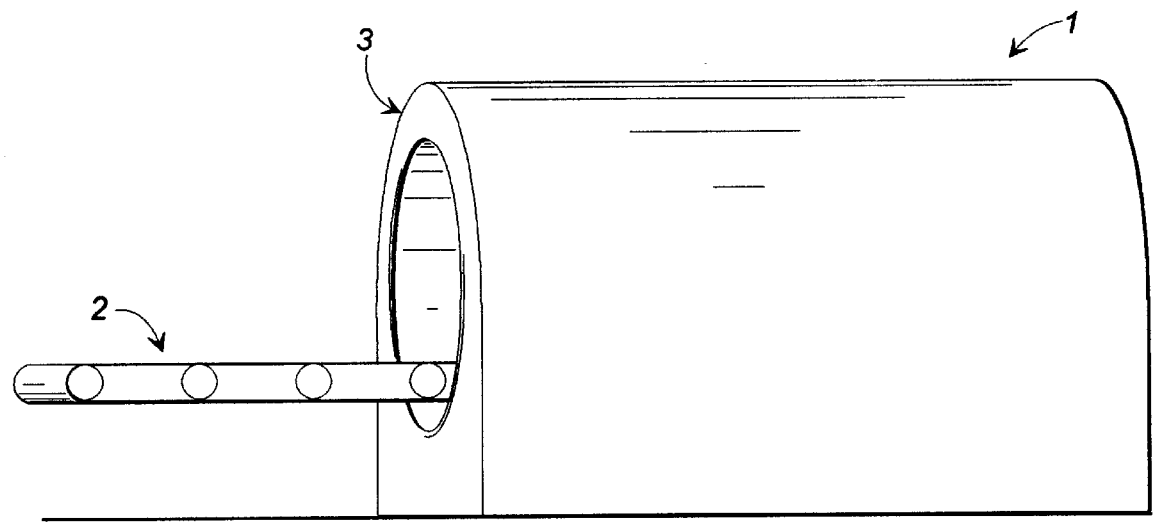
FIG. 1 is a schematic representation of a Magnetic Resonance Imaging (MRI) device.

Referring to FIG. 1 of the drawings, a conventional MRI device 1 is shown. A patient is transported into the tubular MRI device on platform 2 via tubular end 3. Once inside the device, magnetic imaging of the patient is generated to be used by a medical team during subsequent surgery. As can be seen from FIG. 1, it is not possible to perform a surgical procedure and obtain magnetic imaging at the same time using a conventional MRI device.

Figure 2:
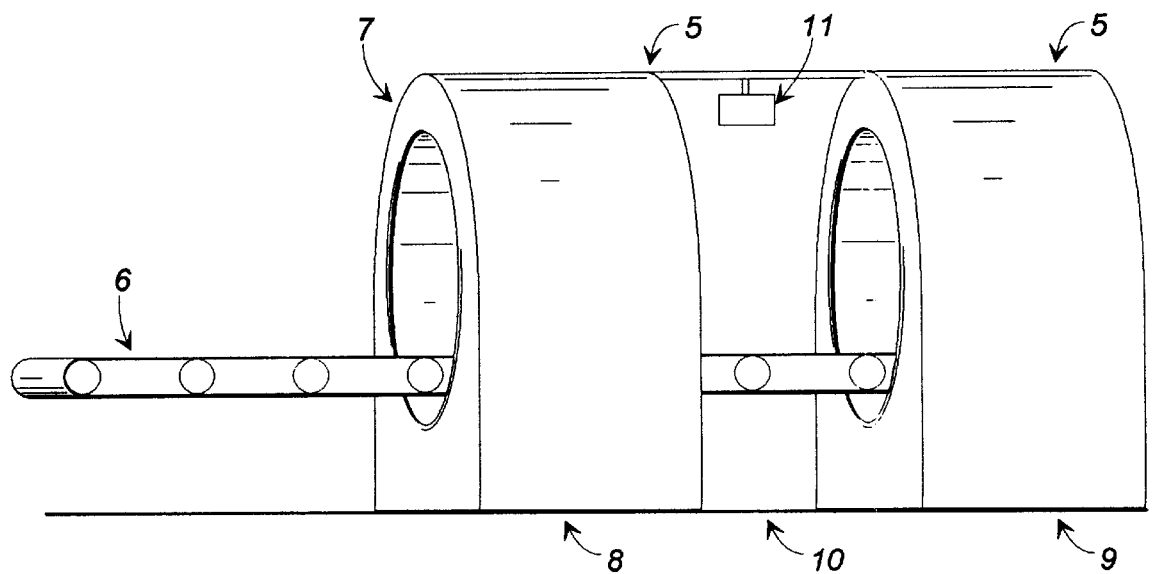
FIG. 2 is a schematic representation of an Interventional Magnetic Resonance Imaging (IMRI) device.

FIG. 2 illustrates an IMRI device 5. A patient is transported into the tubular IMRI device on platform 6 via tubular end 7. A portion of the patient is accessible between magnets 8 and 9, through gap 10. Once inside the IMRI device, magnetic imaging of the patient is generated and displayed on at least one overhead monitor 11, which is used by a medical team performing real-time surgery. As can be seen from FIG. 2, the IMRI device makes it possible to perform a surgical procedure using real-time magnetic imaging data, unlike conventional MRI devices.

Figure 3:
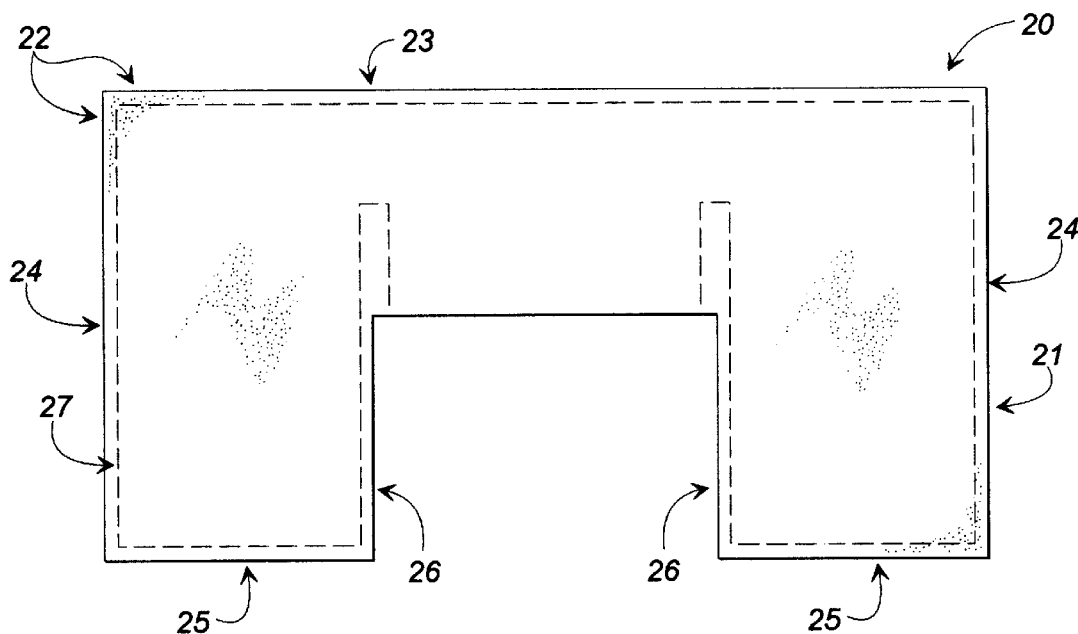
FIG. 3 is a schematic representation of a U-shape equipment drape of the present invention.

The present invention is directed to equipment drapes for use with an IMRI device. FIG. 3 illustrates one equipment drape 20 of the present invention. Equipment drape 20 comprises a U-shape sheet 21 having a peripheral edge 22, wherein the peripheral edge includes an outer upper edge 23, two outer side edges 24, two outer lower edges 25, and two inner side edges 26. The drape also has an adhesive strip 27 along at least a portion of the peripheral edge. Desirably, the adhesive strip is along the entire peripheral edge of the drape.

Figure 4:
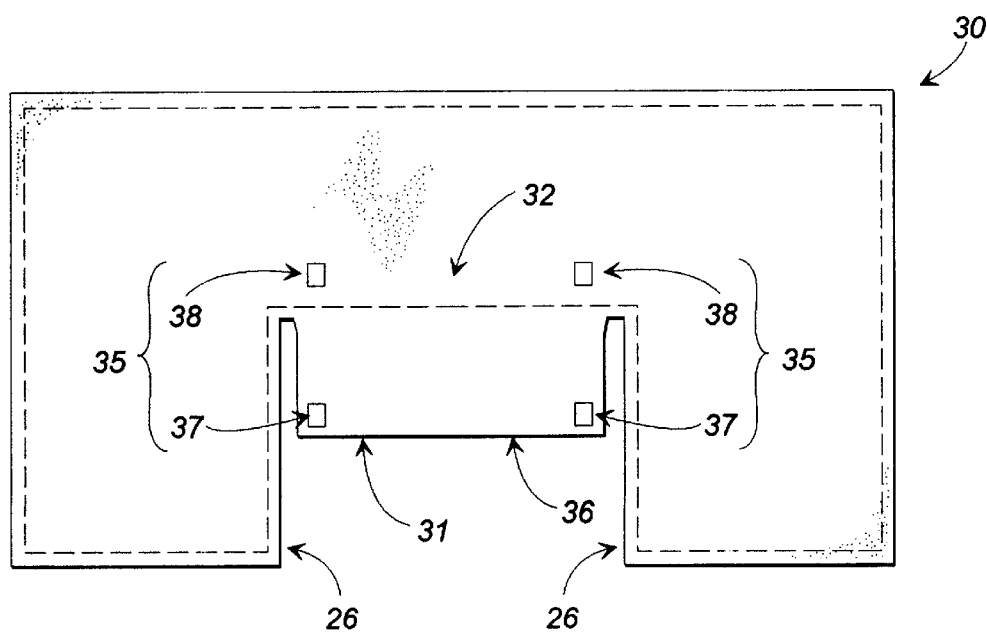
FIG. 4 is a schematic representation of a U-shape equipment drape of the present invention having a flap portion attached to the drape.

FIG. 4 illustrates a variation of the above equipment drape. In this embodiment, an equipment drape 30 is disclosed, wherein the drape further comprises a flap portion 31, which extends downward from a central portion 32 of the drape 30, between the two inner side edges 26. In this embodiment, the drape also has an adhesive strip along at least a portion of the peripheral edge. Desirably, the adhesive strip is along the entire peripheral edge of the drape except for the lower edge of the flap portion.

Figure 5:
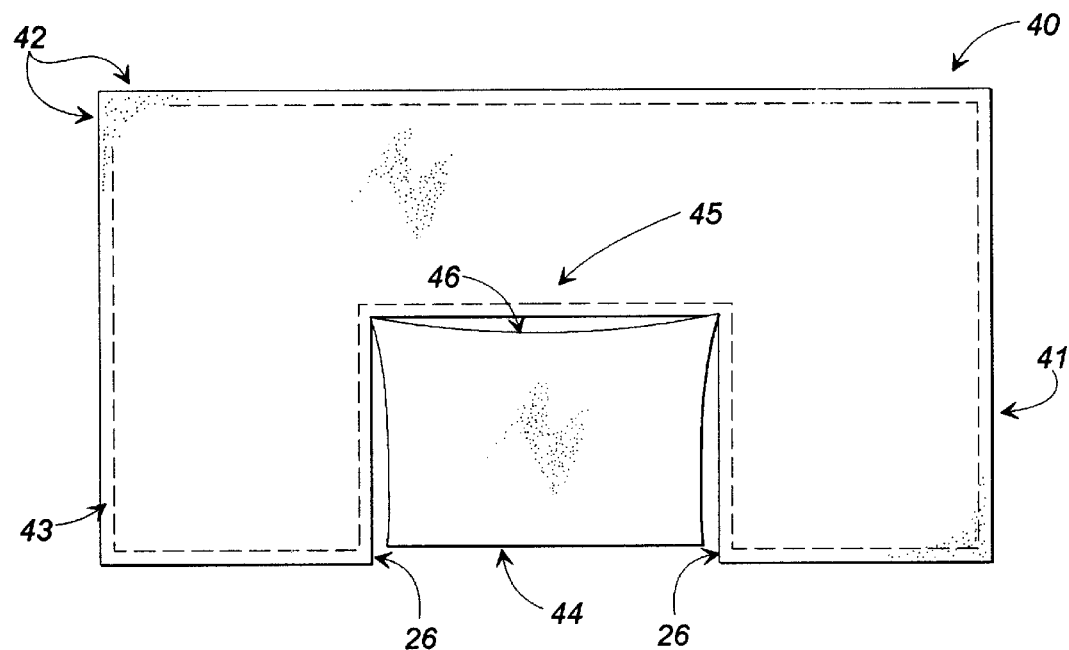
FIG. 5 is a schematic representation of a U-shape equipment drape of the present invention having a pouch attached to the drape.

FIG. 5 illustrates a further embodiment of the present invention. In this embodiment, an equipment drape 40 is disclosed, which comprises a U-shape sheet 41 having a peripheral edge 42 and an adhesive strip 43 along at least a portion of the peripheral edge 42 as above. In this embodiment, the drape 40 further comprises a pouch 44 connected to the U-shape sheet 41, which extends from a central portion of the drape 45 between the two inner side edges 26. The pouch 44 has a pouch opening 46 facing toward the sheet, which can be used to temporarily store surgical instruments during surgery.

Figure 6:
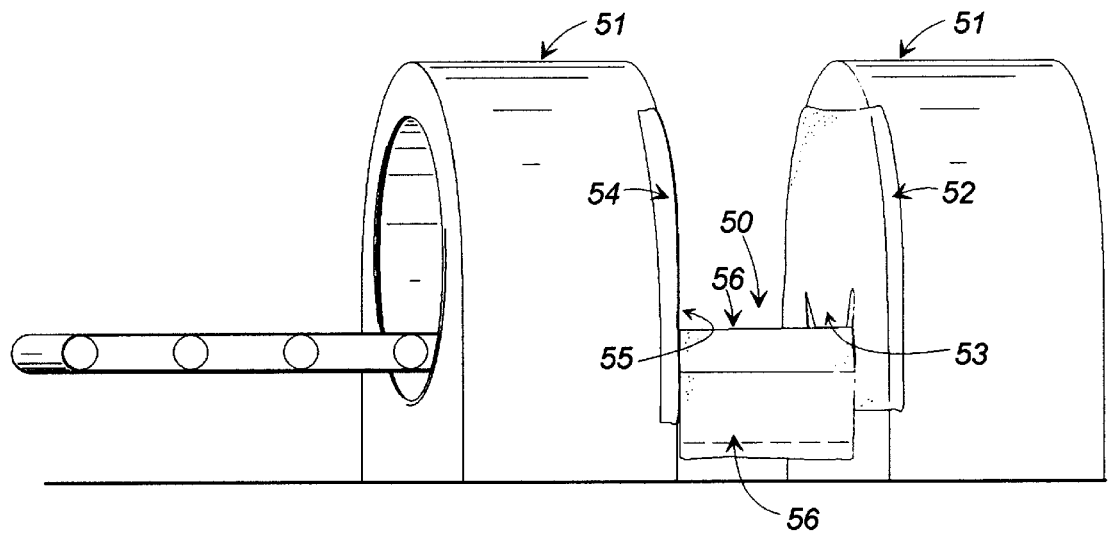
FIG. 6 is a schematic representation of an equipment drape set including a U-shape equipment drape having a pouch attached to the drape, a U-shape equipment drape having a flap portion attached to the drape, and two rectangular equipment drapes on either side of a patient.

FIG. 6 illustrates a further embodiment of the present invention. In this embodiment, an equipment drape set surrounds a "surgery zone" 50, which is produced by attaching four equipment drapes to the IMRI device 51 such that at least a portion of a patient within the IMRI device 51 is partially separated from the surgical team. The four drapes include a U-shaped equipment drape 52, optionally having a flap portion 53, a U-shaped equipment drape 54 having a flap or pouch 55, and two rectangular equipment drapes 56, each of which are positioned between the U-shaped equipment drapes to form the surgery zone 50.

The equipment drapes of the present invention can be made from a variety of substrates including, but not limited to, woven fabrics, nonwoven fabrics, knit fabrics, films, and combination thereof. Desirably, the equipment drapes of the present invention are formed from one or more fabric layers of fabric. In the case of multiple layers, the layers are generally positioned in a juxtaposed or surface-to-surface relationship and all or a portion of the layers may be bound to adjacent layers. In the case of nonwoven fabrics, the nonwoven fabric may also be formed from a plurality of separate nonwoven webs wherein the separate nonwoven webs are similar or different from one another.

As used herein, the term "nonwoven fabric" refers to a fabric that has a structure of individual fibers or filaments which are randomly and/or unidirectionally interlaid in a mat-like fashion. Nonwoven fabrics can be made from a variety of processes including, but not limited to, air-laid processes, wet-laid processes, hydroentangling processes, staple fiber carding and bonding, and solution spinning. Suitable nonwoven fabrics include, but are not limited to, spunbonded fabrics, spunlaced fabrics, meltblown fabrics, wet-laid fabrics and combinations thereof.

As used herein, the term "spunbonded fabric" refers to a web of small diameter fibers and/or filaments which are formed by extruding a molten thermoplastic material, or coextruding more than one molten thermoplastic material, as filaments from a plurality of fine, usually circular, capillaries in a spinnerette with the diameter of the extruded filaments then being rapidly reduced, for example, by non-eductive or eductive fluid-drawing or other well known spunbonding mechanisms. The production of spunbonded nonwoven webs is illustrated in patents such as Appel, et al., U.S. Pat. No. 4,340,563; Dorschner et al., U.S. Pat. No. 3,692,618; Kinney, U.S. Pat. Nos. 3,338,992 and 3,341,394; Levy, U.S. Pat. No. 3,276,944; Peterson, U.S. Pat. No. 3,502,538;

Hartman, U.S. Pat. No. 3,502,763; Dobo et al., U.S. Pat No. 3,542,615; and Harmon, Canadian Patent No. 803,714.

As used herein, the term "spunlaced fabrics" refers to a web of material consisting of a blend of natural fibers and synthetic fibers, where the fibers are subjected to high-velocity water jets which entangle the fibers to achieve mechanical bonding. Desirably, the natural fibers are wood pulp fibers and the synthetic fibers are polyester fibers.

As used herein, the term "meltblown fabrics" refers to a fabric comprising fibers formed by extruding a molten thermoplastic material through a plurality of fine, usually circular, die capillaries as molten threads or filaments into a high velocity gas (e.g. air) stream which attenuates the filaments of molten thermoplastic material to reduce their diameters, which may be to microfiber diameter. Thereafter, the meltblown fibers are carried by the high-velocity gas stream and are deposited on a collecting surface to form a web of randomly disbursed meltblown fibers. The meltblown process is well-known and is described in various patents and publications, including NRL Report 4364, "Manufacture of Super-Fine Organic Fibers" by V.A. Wendt, E. L. Boone, and C. D. Fluharty; NRL Report 5265, "An Improved device for the Formation of Super-Fine Thermoplastic Fibers" by K. D. Lawrence, R. T. Lukas, and J. A. Young; and U.S. Pat. No. 3,849,241 issued Nov. 19, 1974, to Buntin, et al.

As used herein, the term "microfibers" means small diameter fibers having an average diameter not greater than about 100 microns, for example, having a diameter of from about 0.5 microns to about 50 microns. More specifically microfibers may also have an average diameter of from about 1 micron to about 20 microns. Microfibers having an average diameter of about 3 microns or less are commonly referred to as ultra-fine microfibers.

As used herein, the term "wet-laid fabrics" refers to fabrics formed by a process, such as a paper-making process, wherein fibers dispersed in a liquid medium are deposited onto a screen such that the liquid medium flows through the screen, leaving a fabric on the surface of the screen. Fiber bonding agents may be applied to the fibers in the liquid medium or after being deposited onto the screen. Wet-laid fabrics may contain natural and/or synthetic fibers.

Desirably, the equipment drapes of the present invention comprise at least one nonwoven fabric. More desirably, the equipment drapes comprise a spunbonded or spunlaced fabric. Most desirably, the equipment drapes comprise a nonwoven fabric laminate in the form of a spunbonded/meltblown/spunbonded laminate.

The fibrous material used to form the fabrics above include synthetic fibers, natural fibers, and combinations thereof. The choice of fibers depends upon, for example, fiber cost and the desired properties, e.g., liquid resistance, vapor permeability or lint generation, of the finished drape. For example, suitable fibrous materials may include, but are not limited to, synthetic fibers such as those derived from polyolefins, polyesters, polyamides, polyacrylics, etc., alone or in combination with one another. Monocomponent and multicomponent, or conjugate, synthetic fibers may be used alone or in combination with other fibers. Other suitable fibers include natural fibers such as cotton, linen, jute, hemp, cotton, wool, wood pulp, etc. Similarly, regenerated cellulosic fibers such as viscose rayon and cuprammonium rayon, or modified cellulosic fibers, such as cellulose acetate, may likewise be used. Blends of one or more of the above fibers may also be used if so desired.

Monocomponent and conjugate synthetic fibers suitable for the present invention can be produced from a wide variety of thermoplastic polymers that are known to form fibers. Suitable polymers for forming the drapes of the present invention include, but are not limited to, polyolefins, e.g., polyethylene, polypropylene, polybutylene, and the like; polyamides, e.g., nylon 6, nylon 6/6, nylon 10, nylon 12 and the like; polyesters, e.g., polyethylene terephthalate, polybutylene terephthalate and the like; polycarbonates; polystyrenes; thermoplastic elastomers, e.g., ethylenepropylene rubbers, styrenic block copolymers, copolyester elastomers and polyamide elastomers and the like; fluoropolymers, e.g., polytetrafluoroethylene and polytrifluorochloroethylene; vinyl polymers, e.g., polyvinyl chloride, polyurethanes; and blends and copolymers thereof. Particularly suitable polymers for forming the drapes of the present invention are polyolefins, including polyethylene; polypropylene; polybutylene; and copolymers as well as blends thereof. Of the suitable polymers for forming conjugate fibers, particularly suitable polymers for the high melting component of the conjugate fibers include polypropylene, copolymers of polypropylene and ethylene and blends thereof, more particularly polypropylene, and particularly suitable polymers for the low melting component include polyethylenes, more particularly linear low density polyethylene, high density polyethylene and blends thereof; and most particularly suitable component polymers for conjugate fibers are polyethylene and polypropylene.

Suitable fiber forming polymers may additionally have thermoplastic elastomers blended therein. In addition, the polymer components may contain additives for enhancing the crimpability and/or lowering the bonding temperature of the fibers, and enhancing the abrasion resistance, strength and softness of the resulting webs. For example, the low melting polymer component may contain about 5 to about 20% by weight of a thermoplastic elastomer such as an ABA' block copolymer of styrene, ethylenebutylene and styrene. Such copolymers are commercially available and some of which are identified in U.S. Pat. No. 4,663,220 to Wisneski et al. An example of highly suitable elastomeric block copolymers is KRATON G-2740. Another group of suitable additive polymers is ethylene alkyl acrylate copolymers, such as ethylene butyl acetate, ethylene methyl acrylate and ethylene ethyl acrylate, and the suitable amount to produce the desired properties is from about 2 wt. % to about 50 wt. %, based on the total weight of the low melting polymer component. Yet other suitable additive polymers include polybutylene copolymers and ethylene-propylene copolymers.

The equipment drapes of the present invention may be formed from fabrics containing a blend of synthetic fibers and natural fibers. Desirably, the equipment drapes are formed from fabrics containing synthetic fibers in an amount from about 100 to 25 weight percent and natural fibers in an amount from about 0 to 75 weight percent based on the total weight of the fabric. More desirably, the equipment drapes are formed from fabrics containing synthetic fibers in an amount from about 100 to 50 weight percent and natural fibers in an amount from about 0 to 50 weight percent based on the total weight of the fabric. Most desirably, the equipment drapes are formed from fabrics containing synthetic fibers in an amount from about 100 to 90 weight percent and natural fibers in an amount from about 0 to 10 weight percent based on the total weight of the fabric.

It has been found that nonwovens formed from synthetic fibers, alone or in combination with natural fibers, are particularly well-suited for the equipment drapes of the present invention. In particular, synthetic fibers containing a polyolefin are especially suitable for the equipment drapes.

Desirably, the polyolefin fibers are polypropylene or polyethylene fibers. Most desirably, the fibers are polypropylene fibers.

The equipment drapes of the present invention satisfy the need for a suitable equipment drape for use with the recently developed IMRI device. One particularly useful equipment drape is U-shape and has a peripheral edge, wherein the peripheral edge includes an outer upper edge, two outer side edges, two outer lower edges, and two inner side edges. Desirably, the outer upper edge has a length of at least about 270 cm; the two outer side edges have substantially equal lengths of at least about 150 cm; the two outer lower edges have substantially equal lengths of less than about 125 cm; and the two inner side edges have substantially equal lengths of at least about 30 cm. More desirably, the outer upper edge has a length of about 270 to about 280 cm; the two outer side edges have a length of about 150 to about 176 cm; the two outer lower edges have a length of about 95 to about 113 cm; and the two inner side edges have a length of about 80 to about 100 cm. Most desirably, the outer upper edge has a length of about 280 cm; the two outer side edges have a length of about 150 cm; the two outer lower edges have a length of about 113 cm; and the two inner side edges have a length of about 80 cm.

Variations of the above-mentioned equipment drape are within the scope of the present invention. A particularly useful drape comprises the U-shape equipment drape above, wherein the drape further comprises a flap portion which extends downward from a central portion of the drape, between the two inner side edges. Desirably, the flap portion occupies the full width of the area between the two inner side edges of the drape and extends up to the full length of the inner side edges. More desirably, the flap portion extends at least about 10 cm along the inner side edges. Most desirably, the flap portion extends about 10 cm along the inner side edges. The flap portion may be separately formed and subsequently attached to the equipment drape or the flap portion may be an integral part of the equipment drape material. Desirably, the flap portion is formed from materials similar to those disclosed above as suitable materials for the equipment drapes of the present invention. More desirably, the web forming the flap portion is a continuous portion of the web forming the equipment drape. One suitable material for forming the equipment drape and the flap portion is a spunbonded/meltblown/spunbonded nonwoven laminate.

As shown in FIG. 4, the equipment drape 30 and the flap portion 31 may include complementary attachment means 35 for attaching the free end of the flap portion 36 to the drape 30 to maximize the area under the flap portion bounded by the inner side edges 26. Attachment means include, but are not limited to, Velcro strips, plastic snaps, and fabric piles. Desirably, the complementary attachment means include Velcro strips 37 positioned on and extending along each side edge of the flap portion 36 and Velcro negative points 38 extending a length above the flap portion 36 into a central portion 32 of the drape 30. Desirably, the length of the Velcro strips is at least about 1.0 cm; more desirably, the length of the Velcro strips is about 1.0 cm to about full length of the flap portion; and most desirably, the length of the Velcro strips is about 1.5 cm. The length of the Velcro negative points is at least about 1.0 cm; more desirably, the length of the Velcro negative points is about 1.0 cm to about the full length of the flap portion; and most desirably, the length of the Velcro negative points is the full length of the flap portion.

The above-mentioned drape also has an adhesive strip along at least a portion of the peripheral edge. The adhesive strip is present on the side of the drape opposite to the complementary attachment means, if present. Desirably, the adhesive strip is along the entire peripheral edge of the drape, except for the lower edge of the flap, if present. More desirably, the adhesive strip is present along the entire peripheral edge of the drape, except for the lower edge of the flap portion, if present, and also extends beyond the two inner side edges into a central portion of the drape. Most desirably, the adhesive strip extends beyond the two inner side edges into a central portion of the drape a distance equal to twice the length of the flap portion or up to the upper edge of the drape. The width of the adhesive strip along the peripheral edge of the drape may vary depending on the desired degree of adhesion to the IMRI device. Typically, the adhesive strip has a width of about 3 cm to about 10 cm. Desirably, the width of the adhesive strip is about 5 cm.

In a further embodiment, an equipment drape is disclosed which comprises a U-shape sheet having a peripheral edge, an adhesive strip along at least a portion of the peripheral edge, and a pouch connected to the U-shape sheet. The pouch has a pouch opening facing toward the sheet, which can be used to temporarily store surgical instruments during surgery. The pouch extends downward from a central portion of the drape, between the two inner side edges. Desirably, the pouch occupies the full width of the area between the two inner side edges of the drape and extends up to the full length of the inner side edges. More desirably, the pouch extends at least about 50 cm along the inner side edges. Most desirably, the pouch extends the full length of the inner side edges. The pouch may be separately formed and subsequently attached to the equipment drape or the pouch may be an integral part of the equipment drape material. Desirably, the pouch is formed from materials similar to those disclosed above as suitable materials for the equipment drapes of the present invention. More desirably, at least one web forming the pouch is a continuous portion of the web forming the equipment drape. One suitable material for forming the equipment drape and at least one portion of the pouch is a spunbonded/meltblown/spunbonded nonwoven laminate. In this embodiment, a second substrate may be bonded to the SMS laminate to form the pouch. Bonding means are well known to those of ordinary skill in the art and include, but are not limited to, ultrasonic bonding, welding, adhesive bonding, etc.

The pouch-containing equipment drape of the present invention has similar dimensions as the equipment drapes above. Desirably, the outer upper edge has a length of at least about 270 cm; the two outer side edges have substantially equal lengths of at least about 150 cm; the two outer lower edges have substantially equal lengths of less than about 125 cm; and the two inner side edges have substantially equal lengths of at least about 30 cm. More desirably, the outer upper edge has a length of about 270 to about 280 cm; the two outer side edges have a length of about 150 to about 176 cm; the two outer lower edges have a length of about 95 to about 113 cm; and the two inner side edges have a length of about 80 to about 100 cm. Most desirably, the outer upper edge has a length of about 270 cm; the two outer side edges have a length of about 176 cm; the two outer lower edges have a length of about 95 cm; and the two inner side edges have a length of about 100 cm.

The pouch-containing drape also has an adhesive strip along at least a portion of the peripheral edge. Desirably, the adhesive strip is along the upper edge, the two outer side edges, and the two inner side edges of the drape. More desirably, the adhesive strip is present along the upper edge, the two outer side edges, and the two inner side edges of the drape, and also extends between the two inner side edges along an upper edge of the pouch. Most desirably, the adhesive strip is also present along a lower edge of the pouch so that the pouch may be attached to a patient's abdomen during surgery. As discussed above, the width of the adhesive strip along the peripheral edge of the drape may vary depending on the desired degree of adhesion to the IMRI device. Typically, the adhesive strip has a width of about 3 cm to about 10 cm. Desirably, the width of the adhesive strip is about 5 cm.

In a further embodiment, an equipment drape set of the present invention surrounds a "surgery zone", which is produced by attaching four equipment drapes of the present invention to the IMRI device such that a barrier is formed between a portion of a patient within the IMRI device and the surgical team. The four drapes include a U-shaped equipment drape, a U-shaped equipment drape having a flap or pouch, and two square or rectangular equipment drapes, each of which are positioned between the U-shaped equipment drapes to form the surgery zone.

The equipment drape set includes a U-shaped equipment drape attached to an inner surface of the IMRI device at the "head" end of the patient; a U-shaped equipment drape having a flap or pouch attached to an inner surface of the IMRI device at the "feet" end of the patient; and two square or rectangular equipment drapes, each of which are positioned between the U-shaped equipment drapes and on either side of the patient. The two square or rectangular equipment drapes comprise a sheet, desirably formed from materials as described above, having a peripheral edge and an adhesive strip along at least a portion of the peripheral edge. Each square or rectangular equipment drape has an upper edge, a lower edge, and two side edges.

Each square or rectangular equipment drape has dimensions such that, when attached to the IMRI device, the drape forms a barrier between the patient's side and a surgeon. Desirably, the upper and lower edges have substantially equal lengths of at least about 90 cm and the two side edges have substantially equal lengths of at least about 90 cm. Most desirably, the upper and lower edges have substantially equal lengths of about 90 cm and the two side edges have substantially equal lengths of about 90 cm.

The above-mentioned square or rectangular drapes also have an adhesive strip along at least a portion of the peripheral edge. Desirably, the adhesive strip is along the upper edge and at least a portion of the two side edges. More desirably, the adhesive strip is along the upper edge and at least an upper portion of the two side edges. Most desirably, the adhesive strip is along the upper edge and an upper portion of the two side edges, the upper portion of the two side edges having a length of about 30 cm. As discussed above, the width of the adhesive strip along the peripheral edge of the square or rectangular equipment drape may vary depending on the desired degree of adhesion to the IMRI device. Typically, the adhesive strip has a width of about 3 cm to about 10 cm. Desirably, the width of the adhesive strip is about 5 cm.

The equipment drapes of the present invention may be manufactured by any known means of making equipment drapes known to those of ordinary skill in the art. Desirably, the equipment drapes of the present invention are made by the following process, or a variation thereof. The equipment drape is cut from a substrate to produce a drape having a desired shape and desired dimensions. When the drape is U-shape, the drape may be cut, with or without a flap portion. Alternatively, a separately prepared flap portion may be attached to the U-shape equipment drape by any known attachment method. If the U-shape equipment drape is to have a pouch, a second piece of material is bonded to the flap portion, if present, by any known bonding method. Alternatively, a separately prepared pouch may be attached to the U-shape equipment drape by any known attachment method. Then, adhesive is applied to the peripheral edges of the equipment drape. Desirably, the adhesive is covered by a release layer to prevent contamination of the adhesive. If desired, attachment means are connected to the U-shape equipment drape.

The present invention is described above by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

What is claimed is:

1. An equipment drape, for use with an Interventional Magnetic Resonance Imaging device, comprising:
   a U-shape sheet having a peripheral edge, wherein the peripheral edge includes an outer upper edge, two outer side edges, two outer lower edges, and two inner side edges; and
   an adhesive strip along at least a portion of the outer upper edge and the two outer side edges.

2. The equipment drape of claim 1, wherein the sheet comprises a web selected from the group consisting of nonwoven fabrics, woven fabrics, knit fabrics and films.

3. The equipment drape of claim 2, wherein the sheet is a nonwoven fabric selected from the group consisting of meltblown fabrics, spunbonded fabrics, spunlaced fabrics, wet-laid fabrics and combinations thereof.

4. The equipment drape of claim 3, wherein the sheet is a nonwoven fabric comprising a spunbonded/meltblown/spunbonded laminate.

5. The equipment drape of claim 1, wherein the drape further comprises a flap portion which extends from a central portion of the drape along the two inner side edges of the drape.

6. The equipment drape of claim 5, wherein the drape and the flap portion include complementary attachment means for attaching a free end of the flap portion to the drape.

7. The equipment drape of claim 6, wherein the complementary attachment means comprises hook and loop attachment means.

8. The equipment drape of claim 5, wherein a second sheet is attached to the flap portion along three edges of the flap portion to form a pouch, said pouch having a pouch opening facing the central portion of the drape.

9. An equipment drape, for use with an Interventional Magnetic Resonance Imaging device, comprising:
   a U-shape sheet having a peripheral edge, wherein the peripheral edge includes an outer upper edge, two outer side edges, two outer lower edges, and two inner side edges;
   a pouch connected to the sheet and positioned between said two inner side edges, said pouch having a pouch opening facing toward the sheet; and
   an adhesive strip along at least a portion of the peripheral edge.

10. The equipment drape of claim 9, wherein the sheet comprises a web selected from the group consisting of nonwoven fabrics, woven fabrics, knit fabrics and films.

11. The equipment drape of claim 10, wherein the sheet is a nonwoven fabric selected from the group consisting of melt-blown fabrics, spunbonded fabrics, spunlaced fabrics, wet-laid fabrics and combinations thereof.

12. The equipment drape of claim 11, wherein the sheet is a nonwoven fabric comprising a spunbonded/meltblown/spunbonded laminate.

13. The equipment drape of claim 9, wherein the pouch further comprises an adhesive strip along an outer lower edge of the pouch.

14. The equipment drape of claim 9, wherein the pouch comprises a first web joined to a second web to form said pouch.

15. The equipment drape of claim 14, wherein said first web and said sheet are continuous.

16. An equipment drape set, for use with an Interventional Magnetic Resonance Imaging device, comprising:
   (a) a first U-shape sheet having a peripheral edge, wherein the peripheral edge includes an outer upper edge, two outer side edges, two outer lower edges, and two inner side edges; and
   an adhesive strip along at least a portion of the peripheral edge;
   (b) a second U-shape sheet having a peripheral edge, wherein the peripheral edge includes an outer upper edge, two outer side edges, two outer lower edges, and two inner side edges; and
   an adhesive strip along at least a portion of the peripheral edge; and
   (c) two rectangular sheets, each rectangular sheet having a peripheral edge and an adhesive strip along at least a portion of the peripheral edge; said peripheral edge including an upper edge, a lower edge, and two side edges; wherein the first sheet, the second sheet and the two rectangular sheets are attached to an Interventional Magnetic Resonance Imaging device to form a barrier between a surgery zone within the device and a surgical team.

17. The equipment drape set of claim 16, wherein the second U-shape sheet further comprises a flap connected to the second sheet and positioned between said two inner side edges of the second sheet.

18. The equipment drape set of claim 17, wherein the second U-shape sheet and the flap portion include complementary attachment means for attaching a free end of the flap portion to the second U-shape sheet.

19. The equipment drape set of claim 16, wherein the second U-shape sheet further comprises a pouch connected to the second sheet and positioned between said two inner side edges of the second sheet, said pouch having a pouch opening facing toward the second sheet.

20. An equipment drape, for use with an Interventional Magnetic Resonance Imaging device, comprising:
   a U-shape sheet having a peripheral edge, wherein the peripheral edge includes an outer upper edge, two outer side edges, two outer lower edges, and two inner side edges;
   an adhesive strip along at least a portion of the peripheral edge; and
   a flap portion which extends from a central portion of the drape along the two inner side edges of the drape.

* * * * *